(12) United States Patent
Herbig et al.

(10) Patent No.: US 6,406,906 B1
(45) Date of Patent: Jun. 18, 2002

(54) GELATIN MEMBRANE FILTERS AND METHOD FOR PRODUCING THE SAME

(75) Inventors: Helmar Herbig, Göttingen; Helmut Jaschhof, Greifswald; Khuong To Vinh, Bockenem, all of (DE)

(73) Assignee: Sartorius AG (DE)

( * ) Notice: Subject to any disclaimer, the term of this patent is extended or adjusted under 35 U.S.C. 154(b) by 0 days.

(21) Appl. No.: 09/568,774

(22) Filed: May 10, 2000

(51) Int. Cl.[7] .................................................. C12M 1/12

(52) U.S. Cl. .............................. 435/297.1; 435/309.1; 55/522; 55/528; 96/4; 96/12; 96/108; 96/153; 96/154

(58) Field of Search ........................... 435/297.1, 309.1; 55/522, 528; 96/4, 12, 108, 153, 154

(56) References Cited

U.S. PATENT DOCUMENTS

| 4,705,753 A | * 11/1987 | Gregor et al. ............... 435/180 |
| 5,482,753 A | * 1/1996 | Copeland et al. ......... 435/293.1 |
| 5,962,005 A | * 10/1999 | Saga et al. .................... 424/424 |
| 6,165,253 A | * 12/2000 | Sirkar et al. ...................... 96/6 |

FOREIGN PATENT DOCUMENTS

| DE | 11-736-40 | * 7/1964 |

* cited by examiner

*Primary Examiner*—David A. Redding
(74) *Attorney, Agent, or Firm*—Chernoff, Vilhauer, McClung & Stenzel, LLP

(57) ABSTRACT

Membrane filters for the collection and detection of airborne microorganisms are made from gelatin treated with an osmoprotective agent and exhibit the capacity to at least double the number of viable bacteria captured in a given sample relative to conventional gelatin membrane filters.

16 Claims, No Drawings

GELATIN MEMBRANE FILTERS AND METHOD FOR PRODUCING THE SAME

BACKGROUND OF THE INVENTION

The invention concerns gelatin membrane filters for the collection of microorganisms from gases and a process for making such filters.

The gelatin membranes of the invention find utility in the collection of microorganisms from gaseous media such as air, and are particularly suitable for use in the fields of pharmaceuticals, biotech research and development, food and beverage industries, environmental protection, waste management and in equipment for the determination of bacterial counts. In combination with an air microorganism collection device, such membranes permit collection of bacteria, viruses, yeasts and fungi, in order to determine their concentration in a given space. Such monitoring is the first step for the timely introduction of measures to protect persons and products from harm due to an unduly high concentration of microorganisms in, for example, the air of a room.

In special rooms with unusual requirements as to the state of the air, such as in air-conditioned rooms, clean rooms, and intensive care units, the air is regularly checked for its microorganism count. Since, as a general rule, it is filtered air that is tested which by its nature exhibits a low microorganism count, normally large volumes must be tested in order to collect sufficient microorganisms for a reliable report. Air samples are filtered through an appropriately chosen filter such as sterile membrane filters with pore sizes in the microfiltration range. Typically, such filters are of cellulose nitrate, cellulose acetate and gelatin. See, for example, DE 11 73 640. Especially well adapted to the task are gelatin membrane filters, which are generally thought to remain sufficiently moist to be conducive to propagation of retained microorganisms.

Following sampling the microorganism-laden gelatin membrane filters are either placed on an agar growth medium to incubate or stored in a sterile solution such as peptone water or an isotonic saline solution to permit aliquot portions to be incubated later. In the case of deposit on an agar growth medium, out of the collected individual bacterial aggregates, colonies of microorganisms grow while the gelatin membrane filter dissolves and disappears, thus permitting a microorganism count directly on the agar.

When nutrients are supplied to a gelatin membrane filter for growing microorganisms, it has been suggested to add buffering materials, coloring substances chemicals capable of absorbing biologically poisonous materials and/or counteracting traces of heavy metals or even damaging gases contained in the original air sample. See DE 11 73 640 The disadvantage of this is that in spite of the ready supply of nutrients, apparently due to the added substances, substantially fewer detectable colonies propagate from the microorganisms collected on the membrane than were originally present in the contaminated medium, giving a false or inaccurate count.

Thus, a principal aspect of the present invention is the provision of a gelatin membrane filter for the collection of microorganisms from gases, wherein the number of detectable viable microorganisms is substantially increased relative to the number obtainable with known gelatin membrane filters. A closely related aspect is the provision of a process for the manufacture of such a gelatin membrane filter.

BRIEF SUMMARY OF THE INVENTION

Surprisingly, it has been discovered that the number of detectable microorganisms collected on gelatin membrane filters is substantially increased, thereby substantially enhancing bacterial count accuracy, when the gelatin membrane filter contains so-called "osmoprotective" agents such as inositol, betaine, lysine and oxyneurine. Trimethylammonioacetate (TMAA) has been found to be a particularly effective osmoprotective agent insofar as achieving the enhanced and more accurate bacterial count object of the invention.

DETAILED DESCRIPTION OF THE PREFERRED EMBODIMENTS

Contrary to prevailing thought, upon collection by a gelatin membrane filter, a portion of the microorganisms loses so much of its cellular water content that the microorganisms therein are no longer viable, meaning that, upon incubation, no colonies from such a portion can be detected. This phenomenon was discovered from the fact that about half of a known bacteria count for a given sample could be detected when the bacteria-capturing gelatin membrane filter was subjected to nine minutes of air flow instead of the usual one minute. This was not expected, because conventional wisdom was that microorganisms collected on gelatin membrane filters remain moist and able to propagate. See, for example, "Laboratory Filtration, Microbiology, Electrophoresis" page 14, Sartorius GmbH (1984).

In a preferred embodiment of the invention, the gelatin membrane filters contain at least one osmoprotective agent in sufficient amount that the number of viable microorganisms is doubled as compared to gelatin membrane filters not containing such an osmoprotective agent.

The discovery has further been made that the inclusion of an osmoprotective agent in the gelatin membrane filters, when such filters are exposed to a variable through-flow of gases containing a predetermined number of microorganisms, leads to varying portions of viable microorganisms. Trimethylammonioacetate (TMAA) has been found to be a particularly effective osmoprotective agent in the present invention, especially when it is present in the gelatin membrane casting solution in amounts of between 0.005 and 0.75 wt % relative to the gelatin content. The casting solution preferably comprises an aqueous, homogenous solution containing 4.6 to 5.6 wt % gelatin and 38 to 46 wt % ethanol. This makeup is advantageous for promoting stability of the membrane, while the gelatin itself may be stabilized by a binder such as polyvinyl alcohol (PVA) or starch.

Because of the structure of gelatin, it is preferable that the osmoprotective agent is distributed as uniformly as possible throughout the gelatin matrix. If the osmoprotective agent(s) are distributed only on the outer surface of the gelatin membrane matrix, there is a risk that, after lengthy storage, a portion of the osmoprotective agent(s) in the inner matrix migrates away, leading to possible total ineffectiveness. For this reason, the osmoprotective agent(s) are preferably incorporated into the membrane matrix homogenously by means of a phase inversion casting process, whereby the osmoprotective agent(s) are incorporated directly into the membrane casting solution.

Alternatively, the osmoprotective agent(s) can be introduced into the membrane matrix in a fixing or precipitation bath where precipitation of the gelatin membrane filter takes place. Such a precipitation bath preferably comprises methyl acetate containing 10 to 20 wt % of an alcohol, preferably methanol, and up to 2 wt % of the osmoprotective agent(s). At the time of its initial introduction to the precipitation bath, the gelatin membrane is in a partially gelled phase and not yet completely formed, so that the osmoprotective agent(s) can permeate the entire matrix of the membrane.

The gelatin membrane filters of the present invention exhibit a high degree of mechanical stability, as compared to known gelatin membrane filters, such as those disclosed in DE 11 73 640 Because of this advantage, the ability to manipulate such membranes is greatly improved, and at the same time they have an improved air flux by a factor of at least two. Because of this, the subject membranes are particularly well suited for large air through-put for the collection of bacteria, permitting reduction of the amount of time for the collection of microorganisms, and further permitting the testing of gases having an extremely low loading of microorganisms, since greater volumes can be filtered without impairing or destroying the effectiveness of the gelatin membrane filters.

A preferred process for the manufacture of the gelatin membrane filter of the present invention comprises the following steps:

(a) providing an aqueous, substantially homogenous membrane casting solution comprising gelatin, ethanol and at least one osmoprotective agent;

(b) applying a thin film of the casting solution of step (a) to a substrate;

(c) allowing the thin film from step (b) to gel to form a partially gelled membrane;

(d) immersing the partially gelled membrane from step (c) in a precipitation bath to form a gelatin membrane filter; and (e) drying the gelatin membrane filter from step (d).

Alternatively, the osmoprotective agent may be included in the precipitation bath in step (d) instead of in step (a).

In a preferred embodiment of the process, the casting solution contains between 0.005 and 0.75 wt % TMAA relative to the amount of gelatin. In a further embodiment of the invention, in order to increase the mechanical stability of the gelatin membrane filter, 0.02 to 0.1 wt % of a binder such as PVA or starch may be added to the casting solution relative to the total weight of all components of the membrane casting solution.

In a yet another embodiment of the invention, two precipitation baths are used in step (d).

Specifically, a first bath of methyl acetate with 10 to 20 wt % of an alcohol, preferably methanol, is used to initially gel the membrane, where it remains for up to three hours at room temperature. It is then transferred to a second bath of pure methyl acetate for up to three hours at room temperature. Drying, then sterilization, preferably by gamma rays, follow.

EXAMPLE 1

For the fabrication of a gelatin membrane filter, 200 g gelatin (Gelita-Pulvergelatine 250 Bloom, DGF Deutsche Gelatine-Fabriken Stoess AG) and 2 g PVA (Moiwiol Typ 18–88, Hoechst, AG) in 2000 g water were combined and mixed for one hour at 60° C., followed by mixing with 1645 g ethanol and 0.02 g TMAA dissolved in 10 g water. The so-formed casting solution was cooled to 33° C. and a film thereof having a thickness of 350 µm was cast on a substrate at room temperature and ambient relative humidity of 45% and allowed to cool and to gel for five minutes. The partially gelled membrane, together with its substrate, was then transferred to a first precipitation bath comprising methyl acetate and 14 wt % methanol. The membrane remained in this bath for three hours and thereafter was transferred to a second precipitation bath of pure methyl acetate for a period of three hours, whereby complete gelation occurred. The so-formed gelatin membrane was removed from the substrate and dried and was found to have pores of about 3 µm in diameter and an air flux of 138 L/min·cm²·bar.

EXAMPLES 2–4

Three additional gelatin membrane filters were made as in Example 1 with the exception that the wt % of TMAA in the membrane casting solution was varied as noted in Table 1

COMPARATIVE EXAMPLE C

As a control, an additional gelatin membrane filter designated "C" was prepared as in Example 1, but no TMAA was included in the casting solution.

To examine the effectiveness of the L osmoprotective agent, the gelatin membrane filters of Examples 1 through 4 and of Comparative Example C were used to collect identical colony counts of *Escheria coli* ATCC 8739 bacteria for one minute's worth of air flow at 7.5 m³/min. An additional eight minutes of air flow at 7.5 m³/min was pulled through the *E. coli*-treated filters by vacuum. Immediately thereafter, the gelatin membrane filters were placed on agar nutrient plates containing Trypton-Soy-Broth Agar (TSBA). Overnight incubation at 37° C. followed and the number of colonies was determined by microscopic count.

The results are shown in Table 1, which reports the percentage of viable colonies remaining on the filters as compared to the original colony counts. The data reported represent average values from five measurements for each filter with an average deviation of ±8% of each of the percentages of *E. coli* reported, and indicate that treatment of the filters with TMAA led to at least a doubling of the number of viable microorganisms as compared to the count on the gelatin membrane filters which were not treated with this osmoprotective agent (Example C).

TABLE 1

| Example No. | % TMAA | % E. Coli 1 min | % E. Coli 9 min |
|---|---|---|---|
| 1 | 0.01 | 23.3 | 13.0 |
| 2 | 0.05 | 21.0 | 13.2 |
| 3 | 0.25 | 20.8 | 17.7 |
| 4 | 1.0 | 15.2 | 5.8 |
| C | 0 | 8.7 | 4.6 |

The test materials and test methods used in the foregoing Examples a reset forth below.

Test Bacteria

Frozen suspensions of *E. coli* ATCC 8739, used widely in microbiological QS-Departments for pharmaceutical validation examinations, were used with a concentration of ca. $10^3$ colony-building units per mL [KBE/mL]. Two identical parallel stripes of 0.1 mL of thawed suspension were applied on plates containing TSBA. The plates were incubated overnight at 37° C.±2° C. and the bacteria count was microscopically determined by the Gram-Coloration method. The microslide was archived as a reference pattern.

A cultured suspension w a s made by the injection of 50 ml of TSBA in combination with a colony previously cultivated on a plate, in a 250 mL flask. This suspension in the flask was incubated overnight at 37° C. ±2° C. while being shaken in a water bath. The suspension was transferred to sterile flasks and stored at 4° C.±2° C. for further use.

Spores of *Bacillus subtilus* var *niger* (NCTC 10073) were used as a microbiological tracer. These spores were washed three times by centrifugation and reintroduced into a suspension in sterile, distilled water. The concentration of the strain solution of *B. subtilus* was $2 \times 10^9$ KBE/mL. A 1-liter suspension of *B. subtilus* was generated to be added in these tests since the strain solution was diluted to ca. $2.5 \times 10^9$ KBE/mL with sterile, distilled water and heated for 40 minutes to 60° C. so as to kill any vegetative organisms present. The determination of the spore suspension used for the tests yielded a final concentration of B. subtilis spores of $2.26 \times 10^9$ KBE/mL.

Preparation of the Aerosol

The suspension of *E. coli* ATCC 8739 was stored for two weeks at 4° C.±2° C. before its use. A post-use determination by cultivation techniques showed that the *E. coli* concentration had remained constant over the two weeks. Tests were carried out with different concentrations of the test and tracer microorganisms, in order to determine the proper concentration for the final testing.

The concentration of the suspension of E. coli ATCC 8739 was $2.1 \times 10^{10}$ KBE/mL. Synthesis of an aerosol suspension of 10 mL was accomplished by mixing a 5 mL suspension of *E. coli* diluted with distilled water, to bring the concentration to $7.6 \times 10^3$ to $2.8 \times 10^4$ KBE/mL and a 5 ml suspension of *B. subtilis* diluted with distilled water to bring the concentration to $4.0 \times 10^3$ KEE/mL. The final suspension clouded within 30 minutes.

Aerosol Test Apparatus

The aerosol test apparatus included an atomizing apparatus of the collision 3-jet type atomizer for the generation of bacteria aerosols in a sealed chamber. The aerosol chamber was placed in fluid communication with 1-meter-long stainless steel tubing having an inside diameter of 45 mm. This aerosol chamber tubing was connected to the filter head of a Sartorius MD-8 AirScan® air-germ collector by an appropriate adapter. Entry to the chamber of the air-germ collector was protected by a high capacity air filter. The MD-8 AirScan® was then operated in accordance with its instruction manual.

Test Procedure

Nine mL of the suspension to be atomized was placed in the atomizing apparatus with 1 mL retained for a microbiological assay. Each gelatin membrane filter was inserted in its turn into the MD-8 AirScan® filter head.

The MD-8 AirScan® was adjusted to an air through-put of 7.5 m³/h and turned on. After 15 seconds, the atomizing apparatus was activated by putting it into communication with a pressurized gas (180 kPa) line. The atomizing apparatus was operated for one minute and the MD-8 AirScane® was thereafter shut off.

The gelatin membrane filters were laid upon the TSBA plates either immediately after this one-minute exposure to the germ-containing aerosol or laid on the TSEA plates after an additional eight minutes of filtered air and then, as described above, incubated and assayed for viable bacterial colony count.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A gelatin membrane filter for the collection of microorganisms from gases characterized in that said filter contains at least one osmoprotect agent.

2. The filter of claim 1 wherein said osmoprotective agent is trimethylammonioacetate.

3. The filter of claim 1 or 2 containing a binder.

4. The filter of claim 3 wherein said binder is selected from the group consisting of polyvinyl alcohol and starch.

5. A process of making a gelatin membrane filter comprising the steps:
   (a) providing an aqueous, substantially homogenous membrane casting solution comprising gelatin, ethanol and at least one osmoprotective agent;
   (b) applying a thin film of said casting solution of step (a) to a substrate;
   (c) allowing said thin film of step (b) to gel to form a partially gelled membrane;
   (d) immersing said partially gelled membrane of step (c) in a precipitation bath to form a gelatin membrane filter; and
   (e) drying said gelatin membrane filter.

6. The process of claim 5 wherein said agent comprises 0.005 to 0.75 wt % trimethylammonioacetate relative to the amount of the gelatin in said casting solution.

7. The process of claim 5 wherein gelatin and ethanol are present in said casting solution in an amount ranging from 4.6 to 5.6 wt % and from 38 to 46 wt % respectively.

8. The process of claim 5 wherein said casting solution contains from 0.02 to 0.10 wt % binder.

9. The process of claim 8 wherein said binder is selected from the group consisting of polyvinyl alcohol and starch.

10. The process of any of claims 5 to 9 wherein said precipitation bath of step (d) comprises methyl acetate and from 10 to 20 wt % of an alcohol.

11. The process of claim 10 wherein said alcohol is methanol.

12. A process for making a gelatin membrane filter comprising the steps:
   (a) providing an aqueous, substantially homogenous membrane casting solution comprising gelatin and ethanol;
   (b) applying a thin film of said casting solution from step (a) to a substrate;
   (c) allowing said thin film of step (b) to gel to form a partially gelled membrane;
   (d) immersing said partially gelled membrane in a precipitation bath comprising methyl acetate, an alcohol, and trimethylammonioacetate; and
   (e) drying said gelatin membrane filter.

13. The process of claim 12 wherein trimethylammonioacetate is present in said precipitation bath in a concentration of up to 2 wt %.

14. The process of claim 12 wherein said alcohol in step (d) is methanol and is present in said precipitation bath in a concentration of from 10 to 20 wt %.

15. The process of claim 12 wherein said casting solution comprises 0.02 to 0.1 wt % binder.

16. The process of claim 15 wherein said binder is selected from the group consisting of polyvinyl alcohol and starch.

* * * * *

UNITED STATES PATENT AND TRADEMARK OFFICE
CERTIFICATE OF CORRECTION

PATENT NO. : 6,406,906 B1  Page 1 of 1
DATED : June 18, 2002
INVENTOR(S) : Elmar Herbig, Helmut Jaschhof and Khuong To Vinh It is certified that error appears in the above-identified patent and that said Letters Patent is hereby corrected as shown below:

<u>Title page,</u>
Item [75], delete "Helmar" and substitute -- Elmar --.

<u>Column 1,</u>
Line 47, insert -- or -- between "coloring substances" and "capable of".

<u>Column 4,</u>
Line 16, delete the letter "L" prior to "osmoprotective".
Line 48, change "a reset" to -- are set --.

<u>Column 5,</u>
Line 29, change "KEE/mL." to -- KBE/mL. --.
Line 59, change "TSEA" to -- TSBA --.

<u>Column 6,</u>
Line 6, delete "osmoprotect" and insert -- osmoprotective --.
Line 31, insert a comma -- , -- after "46 wt%".

Signed and Sealed this

Ninth Day of September, 2003

JAMES E. ROGAN
*Director of the United States Patent and Trademark Office*